United States Patent
Morita et al.

(10) Patent No.: US 8,535,474 B2
(45) Date of Patent: Sep. 17, 2013

(54) LIQUID APPLICATOR

(75) Inventors: Akio Morita, Tochigi (JP); Satoshi Ueno, Tochigi (JP)

(73) Assignee: Kao Corporation, Tokyo (JP)

( * ) Notice: Subject to any disclaimer, the term of this patent is extended or adjusted under 35 U.S.C. 154(b) by 329 days.

(21) Appl. No.: 12/670,359

(22) PCT Filed: Jul. 29, 2008

(86) PCT No.: PCT/JP2008/063573
§ 371 (c)(1),
(2), (4) Date: Jan. 22, 2010

(87) PCT Pub. No.: WO2009/020012
PCT Pub. Date: Feb. 12, 2009

(65) Prior Publication Data
US 2010/0224318 A1 Sep. 9, 2010

(30) Foreign Application Priority Data

Aug. 6, 2007 (JP) ................................ 2007-204805
Oct. 16, 2007 (JP) ................................ 2007-268872

(51) Int. Cl.
| | |
|---|---|
| *B29C 65/00* | (2006.01) |
| *B32B 37/00* | (2006.01) |
| *B32B 38/14* | (2006.01) |
| *B32B 7/14* | (2006.01) |
| *B05C 11/02* | (2006.01) |
| *B05C 1/00* | (2006.01) |

(52) U.S. Cl.
USPC ............ 156/277; 156/291; 118/118; 118/244

(58) Field of Classification Search
USPC ............. 156/60, 90, 277, 290, 291, 295, 324,
156/349, 384, 387, 502, 504, 538, 539, 543,
156/547, 548, 549, 578; 118/100, 110, 114,
118/116, 117, 118, 200, 244, 248, 249
See application file for complete search history.

(56) References Cited

U.S. PATENT DOCUMENTS

| 2,546,304 A | 3/1951 | Huebner |
| 3,002,449 A | 10/1961 | Sherman |
| 4,770,909 A | 9/1988 | McIntyre |

FOREIGN PATENT DOCUMENTS

| DE | 1115120 B | 10/1961 |
| DE | 19505978 A1 * | 8/1995 |

(Continued)

OTHER PUBLICATIONS

English translation of International Preliminary Report on Patentability (Form PCT/IB/338 and 373) and of Written Opinion of International Searching Authority (Form PCT/ISA/237) mailed on Mar. 4, 2010 in PCT/JP2008/063573.

(Continued)

*Primary Examiner* — Philip Tucker
*Assistant Examiner* — Brian R Slawski
(74) *Attorney, Agent, or Firm* — Birch, Stewart, Kolasch & Birch, LLP

(57) ABSTRACT

A liquid applicator having a discharge roller (3) that discharges a liquid fed from feeding means in a prescribed pattern. The liquid discharged from the discharge roller (3) is applied to a moving substrate (S). The discharge roller (3) includes a surface plate (31) and a roller main body (32). The roller main body (32) has on its peripheral portion a recess (33) of prescribed shape, in which a liquid is introduced through the inside of the roller main body (32) and spread along the surface of the surface plate (31). The surface plate (31) has, in its portion covering the recess (33), a liquid exit part (3b) that permits exit of the liquid in a pattern different from the opening shape of the recess (33) and a liquid block part (3c) that blocks passage of a liquid. The liquid exit part (3b) is formed of a porous material having a large number of fine pores.

4 Claims, 12 Drawing Sheets

(56) References Cited

FOREIGN PATENT DOCUMENTS

| | | |
|---|---|---|
| DE | 19505978 A1 | 8/1995 |
| EP | 0 745 433 A1 | 12/1996 |
| EP | 745433 A1 * | 12/1996 |
| JP | 123105 C2 | 1/1938 |
| JP | 8-257462 A | 10/1996 |
| JP | 08257462 A * | 10/1996 |
| JP | 9-299849 A | 11/1997 |
| JP | 09299849 A * | 11/1997 |
| JP | 11-506367 | 6/1999 |
| JP | 2000-317383 A | 11/2000 |
| JP | 2003-508276 A | 3/2003 |

OTHER PUBLICATIONS

Extended European Search Report dated Jun. 6, 2012, for European Application No. 08791808.2.

Chinese Office Action for Application No. 200880024657.4 dated May 11, 2012 (with English translation).

English computer-generated translation of JP-123105-C2, published on Jan. 12, 1938.

* cited by examiner

Fig.4(a)
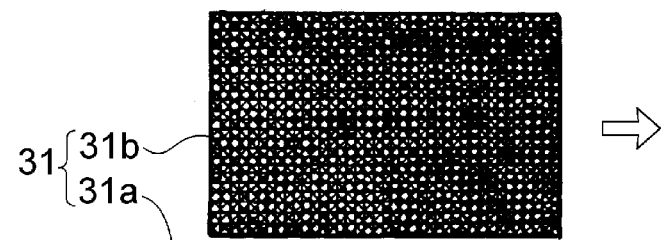
Fig.4(b)
Fig.4(c)
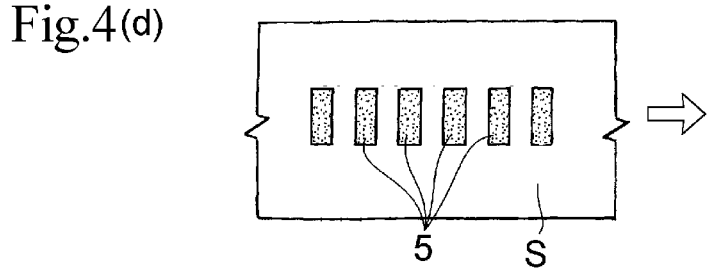
Fig.4(d)
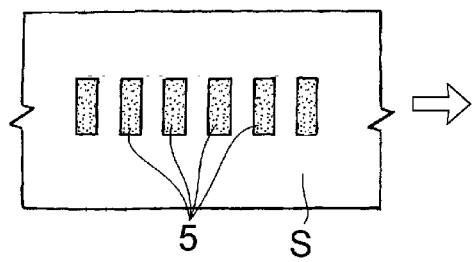

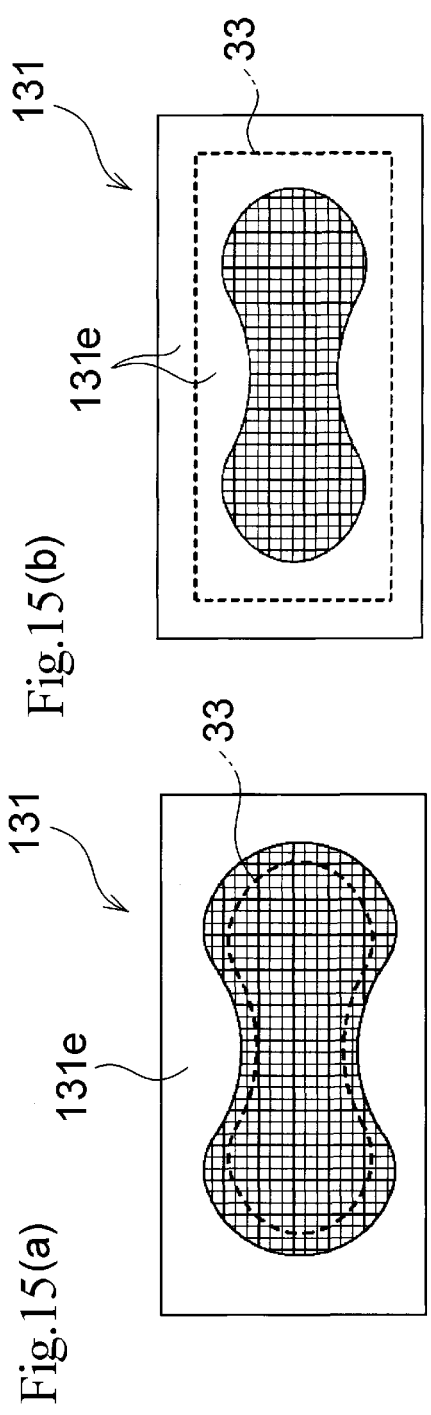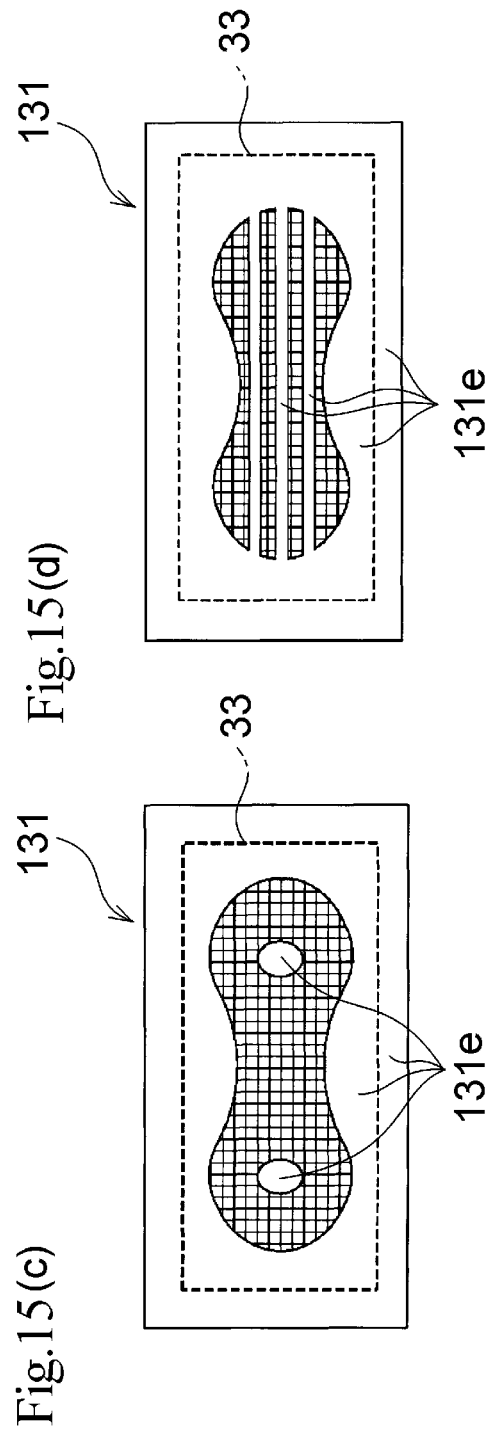

LIQUID APPLICATOR

TECHNICAL FIELD

The present invention relates to a liquid applicator.

BACKGROUND ART

Known apparatus for applying an adhesive include a fluid applicator including a porous roller having a porous cylinder on its outer peripheral surface, through which a liquid such as a hot melt adhesive is forced out and applied to a moving web (see U.S. Pat. No. 4,770,909, hereinafter patent document 1).

JP 9-299849 A (hereinafter, referred to as patent document 2) discloses an adhesive applicator for applying an adhesive to a moving substrate in a prescribed pattern. The applicator includes a pattern cylinder having a plurality of discharge holes corresponding to the prescribed pattern and a driving drum installed inside the pattern cylinder. A hot melt adhesive supplied from feeding means is discharged through the holes of the pattern cylinder in the prescribed pattern and transferred onto a moving substrate via transfer means.

According to the technique of patent document 2, a hot melt adhesive fed from feeding means is once stored in the recesses formed on the inner side of the pattern cylinder and then forced through the discharge holes of the pattern cylinder.

Patent document 2 mentions that, the hot melt adhesive being once stored in the recesses and then emitted from the holes, pressure is evenly imposed to the hot melt adhesive, which enables more stable pattern coating.

DISCLOSURE OF THE INVENTION

The porous cylinder used in the apparatus of patent document 1 is constructed of sintered metal. The pore size of sintered metal is decided by the alignment of metal grains during quenching. Therefore, the resulting porous cylinder has fine pores and coarse pores. Such a porous cylinder formed of sintered metal allows only a smaller amount of a liquid to pass through the fine pores and a larger amount of a liquid to pass through the coarse pores, resulting in uneven application of a liquid such as an adhesive. In applying an adhesive as a liquid, uneven application leads to non-uniform adhesive strength.

In the case of the apparatus of patent document 2, non-uniformity or variation in the amount of an adhesive discharged from the discharge holes of the pattern cylinder can occur. Furthermore, because the holes are made through a pattern cylinder having a certain thickness, it is difficult to make small holes, resulting in a failure to meet the demand for fine and complicated pattern coating.

The present invention provides, in its first aspect, a liquid applicator including a discharge roller that discharges a liquid fed from feeding means in a prescribed pattern. The liquid discharged from the discharge roller is applied to a moving substrate. The discharge roller includes a surface plate as an outer peripheral portion thereof and a roller main body as portion radially inward of the surface plate. The roller main body has in its peripheral portion a recess of prescribed shape, in which a liquid introduced therein through the inside of the roller main body spreads along the surface of the surface plate. The surface plate has in its portion covering the recess a liquid exit part that permits exit of the liquid in a pattern different from the opening shape of the recess and a liquid block part that blocks passage of a liquid. The liquid exit part is formed of a porous material having a large number of fine pores.

The present invention also provides, in its second aspect, a liquid applicator including a discharge roller having a surface plate. The discharge roller discharges a liquid fed from feeding means through the surface plate. The liquid discharged from the discharge roller is applied to a moving substrate. The surface plate has a stack structure composed of a plurality of porous materials superposed one on top of another.

The present invention also provides a method of producing an absorbent article having, on its side to be brought into contact with a garment, a pressure-sensitive adhesive layer formed by applying an adhesive. The absorbent article is adapted to be attached to a garment via the pressure-sensitive adhesive layer. The method includes the step of applying an adhesive to a sheet material providing the side to be brought into contact with a garment by using the above described liquid applicator wherein the liquid is an adhesive.

The invention also provides a method of producing an absorbent article including the step of applying an adhesive to a component of an absorbent article using the above described liquid applicator wherein the liquid is an adhesive and the step of joining the component to other component via the adhesive.

BRIEF DESCRIPTION OF THE DRAWING

FIG. 4(a) is a view of a porous plate used in the embodiment, seen from its normal direction; FIG. 4(b) is a view of a pattern plate used in the embodiment, seen from its normal direction; FIG. 4(c) is a view of a recess used in the embodiment, seen from the normal direction of the bottom of the recess; and FIG. 4(d) is a plan of a web on which a liquid (adhesive) has been applied in a pattern in the embodiment.

FIG. 15(a), FIG. 15(b), FIG. 15(c), and FIG. 15(d) are each a plan of a surface plate used in other embodiments of the liquid applicator according to the second aspect of the invention.

BEST MODE FOR CARRYING OUT THE INVENTION

The present invention relates to a liquid applicator used to apply a liquid such as an adhesive to a substrate in a prescribed pattern and capable of applying a liquid uniformly over the whole area to be coated of a substrate.

The invention also relates to a liquid applicator capable of applying a liquid such as an adhesive uniformly.

The present invention will be described based on its preferred embodiments with reference to the accompanying drawing.

A first embodiment of the liquid applicator according to the first aspect of the invention is described first.

Figure 1:
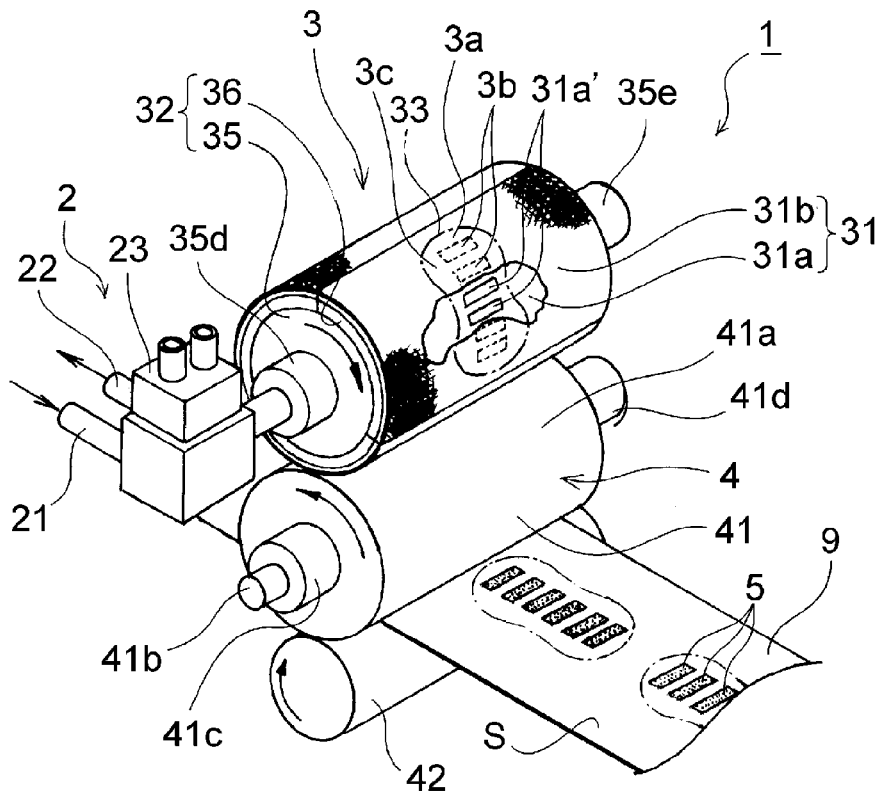
FIG. 1 is a perspective of an essential part of an embodiment of the liquid applicator according to the first aspect of the invention.

FIG. 1 is a perspective of an essential part of an embodiment of the liquid applicator according to the first aspect of the invention (hereafter referred to as an applicator 1).

The applicator 1 is used to apply a hot melt adhesive. The applicator 1 includes feeding means 2 for feeding a hot melt adhesive, an discharge roller 3 that discharges a hot melt adhesive fed from the feeding means 2 in a prescribed pattern, and transfer means 4 for transferring the hot melt adhesive discharged from the discharge roller 3 in a prescribed pattern onto the surface of a continuously fed web (substrate) S.

The feeding means 2 has a tank (not shown) storing a hot melt adhesive, a feed pipe 21 connecting the tank and the discharge roller 3, a pump (not shown) fitted in the feed pipe 21, a return pipe 22 branched from the feed pipe 21, and a control valve 23 switching the hot melt adhesive flow from the feed pipe 21 between the return pipe 22 and the discharge roller 3.

Figure 2:
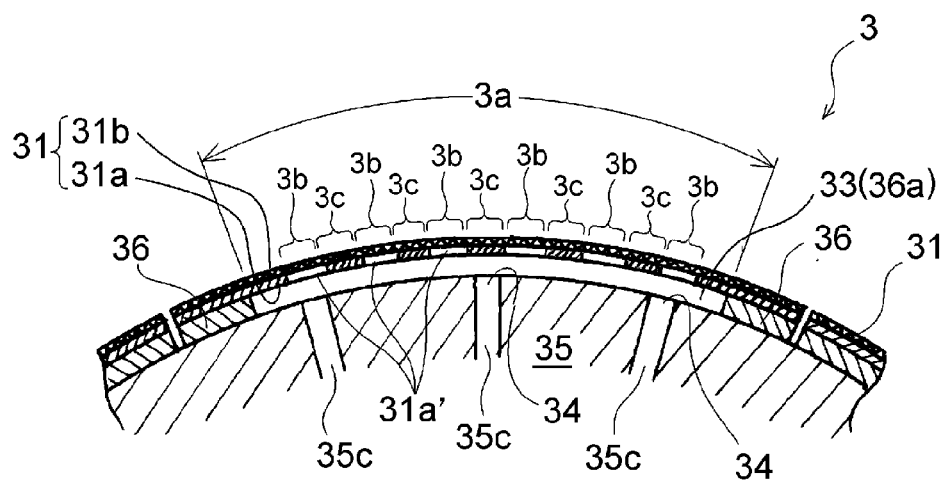
FIG. 2 is a cross-section of an essential part of a discharge roller used in the embodiment, displaying the structure of the outer periphery of the discharge roller.

As illustrated in FIGS. 1 and 2, the discharge roller 3 includes a surface plate 31 forming the outer peripheral portion of the discharge roller 3 and a roller main body 32 constructing the portion radially inward of the surface plate 31 (the portion proximal to the rotational axis).

The roller main body 32 has a columnar shape having, on its peripheral surface, a plurality of recesses 33 arranged at intervals in the circumferential direction. Each of the recesses 33 is formed by providing a level difference from the other portion. The bottom of the recess 33 is provided with inlets 34 for introducing a hot melt adhesive into the recess 33. The surface plate 31 is fixed to the outer peripheral surface of the roller main body 32 to cover the recess 33.

Figure 3:
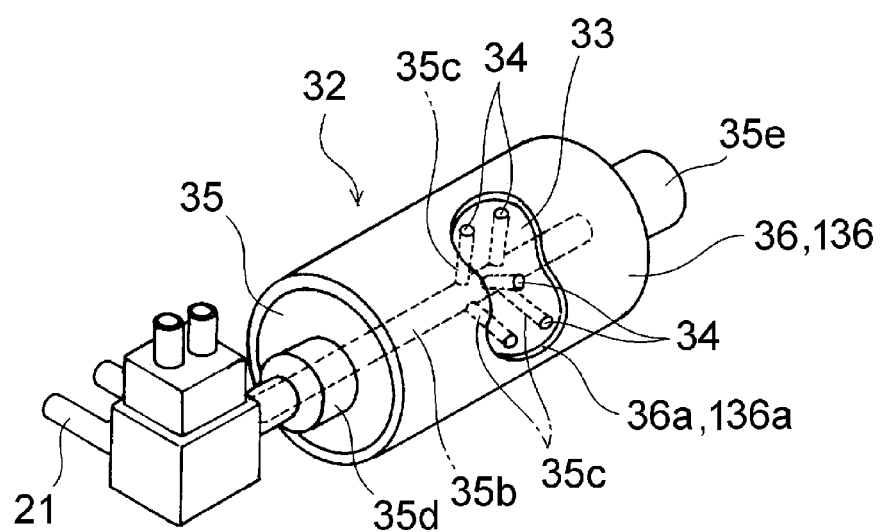
FIG. 3 is a perspective of a roller main body commonly used in the liquid applicators illustrated in FIGS. 1 and 5.

As illustrated in FIGS. 2 and 3, the roller main body 32 includes a body 35 constituting the part of the roller main body 32 proximal to the rotational axis and a plurality of recess-forming plates 36 fixed to the outer peripheral surface of the body 35.

Each of the recess-forming plates 36 has a hole 36a through its thickness. With the recess-forming plate 36 fitted on the body 35, the inner circumferential wall of the hole 36a and the outer periphery of the body 35 form a recess 33.

The recess 33 has an opening on the side opposite to the body 35 with respect to its depth direction (the thickness direction of the plate 36), and the shape of the opening in a plan view is the opening shape of the recess 33. In an assembly as a discharge roller 3, the opening of the recess 33 is covered with the surface plate 31 as illustrated in FIG. 2.

The body 35 has a columnar shape with the inlets 34 formed on its outer peripheral surface. All the recess-forming plates 36 are fixed in a configuration that the inlets 34 may be located within the holes 36a.

The recess 33 may have any three-dimensional shape (prescribed shape) as long as a liquid introduced through the inlets 34 into the recess 33 is allowed to spread along the planar directions of the surface plate 31 (i.e., the circumferential direction and the axial direction of the discharge roller 3).

The recess-forming plates 36 are fixed to the outer peripheral surface of the body 35 in series in the peripheral direction of the body 35. Thus, the recess-forming plates 36 define the outer periphery of the cylindrical roller main body 32. The surface plates 31 are fixed to the outer periphery of the roller main body defined by the recess-forming plates 36. Each surface plate 31 is fixed at a position such that the recess 33 formed by the hole 36a of the recess-forming plate 36 is totally covered therewith. Each of the surface plates 31 used in the applicator 1 is detachably fixed to each of the recess-forming plates 36 with a fastener such as a bolt. Each of the recess-forming plates 36 is also detachably fixed to the body 35 with a fastener such as a bolt. The fastener for fixing the recess-forming plate 36 to the body 35 may double as a fastener for fixing the surface plate 31 to the recess-forming plate 36. Fixing the recess-forming plate 36 to the surface plate 31 may precede fixing to the body 35. The surface plate 31 may have a length extending the whole periphery of the roller main body 32. In this case, a single surface plate 31 is removably fitted over the body 35 having the recess-forming plates 36 fixed thereto.

As illustrated in FIG. 3, the roller main body 32 has in its core a main conduit 35b extending in the rotation axial direction of the discharge roller 3, through which a hot melt adhesive fed from the feed pipe 21 flows. The roller main body 32 also has inside a plurality of branched conduits 35c interconnecting the main conduit 35b and the inlets 34. A hot melt adhesive fed through the feed pipe 21 of the feeding means 2 flows through the main conduit 35b and the branched conduits 35c and enters the recess 33 through the inlets 34. The hot melt adhesive spreads in the recess 33 in directions along the surface of the surface plate 31 (almost parallel to the plane of the surface plate 31) and then exits through the pores of the surface plate 31 out of the surface of the discharge roller 3. The directions along the surface of the surface plate 31 can be said to be directions perpendicular to the depth direction of the recess 33. The phrase "spread in directions along the surface of the surface plate 31" means to spread in at least said directions and is not intended to exclude spreading in a direction perpendicular to the surface of the surface plate 31 (i.e., the depth direction of the recess) simultaneously with the spread in said directions.

As illustrated in FIGS. 1 and 2, the surface plate 31 in the applicator 1 has, in its portion 3a covering the recess 33, liquid exit parts 3b that permit the liquid to exit in a pattern different from the opening shape of the recess 33 and liquid block parts 3c that block passage of a liquid.

The liquid exit part 3b is a part where a liquid is allowed to pass through the thickness of the surface plate 31, which is also a part other than the liquid block part 3c of the recess-covering portion 3a of the surface plate 31.

The shape of the liquid exit part 3b is decided according to a desired shape of a liquid-coated area 5 on a substrate S. In the present embodiment, as shown in FIGS. 1 and 4, the liquid is applied to make a rectangular coated area, so that the individual liquid exit parts 3b have the same rectangular shape as the liquid-coated area 5.

The phrase "discharge a liquid in a pattern different from the opening shape of the recess 33" means that the shape of the liquid forced out of the surface of the discharge roller, which corresponds to the shape of the liquid-coated area 5, depends not on the opening shape of the recess 33 but on the shape of the liquid exit part 3b. Even when the opening shape of the recess 33 and the plan view shape of the liquid exit part 3b are similar to each other, they are different in shape. In other words, the opening shape of the recess 33 and the plan view shape of the liquid exit part 3b are not the same.

The size (area) of the individual liquid exit parts 3b is selected as appropriate to a desired size of a liquid-coated area 5 to be formed on a substrate S. It may range, for example, 0.005 to 10,000 cm². In the cases where an attachment layer (a pressure-sensitive adhesive layer) is formed on the skin contacting surface of sanitary napkins, panty lines, and the like for the attachment to panties, etc., the size (area) of the individual liquid exit parts 3b is preferably 0.005 to 500 cm².

In FIG. 4, the outline arrows indicate the rotation direction of the discharge roller 3 or the moving direction of the substrate S.

The surface plate 31 of the applicator 1 has a plurality of the liquid exit parts 3b in its portion 3a covering the recess 33. The plurality of the liquid exit parts 3b are arranged discretely with the liquid block part 3c therebetween. When there are a plurality of liquid exit parts 3b per the portion 3a, since a liquid spreads in the recess 33 smoothly, the surface plate 31 is capable of discharging a constant amount of the liquid evenly from the liquid exit parts 3b. In the example illustrated in FIGS. 1 and 4, six liquid exit parts 3b are formed per recess 33.

The individual liquid exit parts 3b of the surface plate 31 are formed of a porous material with numerous fine pores. The pore of the porous material is significantly smaller than the liquid exit part 3b. Examples of the porous material that can be used in the invention include a metal mesh, an etched porous plate, punching metal, ceramics, sintered metal, and composites of these materials.

The porous material forming the liquid exit part 3b preferably has an average pore size of 0.05 to 2 mm, more preferably 0.07 to 0.8 mm, and an opening area ratio of 1% to 80%, more preferably 10% to 60%. The area of the individual pores is preferably 0.002 to 3.2 mm², more preferably 0.004 to 0.5 mm². The number of the pores per liquid exit part 3b is at least 3.

The average pore size and pore area of the porous material are measured as follows. A surface plate 31 is observed from right above with an optical microscope to measure the area S of at least 10 openings as observed on the surface of the plate. The measured values are substituted for S in expression: $S=\pi/4 \times d^2$ ($\pi=3.14$) to calculate d's, which are averaged to give a circular equivalent diameter. The pore area is easily measured by encircling an arbitrarily chosen dot on the image as observed using, for example, a digital HD microscope VH-7000 from Keyence.

As illustrated in FIG. 4, the surface plate 31 of the applicator 1 is composed of a pattern plate 31a having holes 31a' which shape is different from the opening shape of the recess 33, and a porous plate 31b having a number of fine pores that is overlaid on the holes 31a' of the pattern plate 31a. The pattern plate 31a decides the liquid discharge pattern. The porous plate 31b is formed of the above described porous material. The part of the porous plate 31b that covers the hole 31a' of the pattern plate 31a becomes the liquid exit part 3b, while the part of the porous plate 31b that overlies other than the holes 31a' of the pattern plate 31a (i.e., non-hole area) makes the liquid block part 3c of the surface plate 31 in combination with the non-hole area of the pattern plate 31a.

The porous plate 31b and the pattern plate 31a in the present embodiment are bonded together by welding, sintering, adhesive application, or like means in the area except the holes 31a'. The pattern plate 31a can be of metal, resins, etc. For example, a stainless sheet with openings of prescribed shape, punching metal, an etched porous material, or a polyester mesh can be used. A polyester mesh can be masked by a post-treatment.

The porous plate may be a stack of the above recited porous materials.

Of the components making the surface plate 31 used in the present embodiment, the porous plate 31b is outside the pattern plate 31a, defining the outermost surface of the discharge roller 3. The outermost surface being formed of the porous plate 31b, the discharge roller 3 has a uniform surface with little level difference, which improves the processing stability in continuous application.

In the present embodiment, the recess 33 has a constant depth (equal to the distance between the bottom 35a of the recess 33 and the surface plate 31) over the entire area thereof. The depth of the recess 33 is preferably 0.1 to 5.0 mm, more preferably 0.5 to 3.0 mm.

The number of the inlets 34 to be provided in the recess 33 is preferably one per 0.5 to 10 cm² of the bottom area of the recess 33.

The overall thickness of the surface plate 31 is preferably 2 mm or less, more preferably 1 mm or less, even more preferably 0.3 to 0.9 mm, to secure even application over the entire area of a substrate to be coated. For the same viewpoint, the overall thickness of the surface plate 31 is preferably 0.05 to 20 times, more preferably 0.1 to 2 times, the depth of the recess 33.

The body 35 of the roller main body 32 has, at one axial end thereof, a tubular member 35d rotatably connected to the end of the feed pipe 21 of the feeding means 2 and, at the other end, an axial member 35e connected to a drive shaft of a drive source (not shown). The body 35 of the roller main body 32 has a heater (not shown) such as a cartridge heater inside of it, whereby the temperature inside the roller main body 32 is adjusted to control the viscosity of the hot melt adhesive flowing there.

The transfer means 4 includes a transfer roller 41 that rotates in contact with the outer peripheral surface, which is formed of the surface plate 31, of the discharge roller 3 and the web S, and a nip roller 42 that is placed beneath the transfer roller 41, between which the web S is moved.

The transfer roller 41 has its outer peripheral surface 41a lined with a release material such as silicone rubber so that the discharged hot melt adhesive may easily be released and transferred onto the substrate. The transfer roller 41 has inside thereof a conduit line (not shown) so that cooling water is circulated through a water conduit 41b to maintain the transfer roller 41 at low temperatures. The transfer roller 41 has at one axial end thereof a tubular member 41c rotatably connected to the water conduit 41b and, at the other end, an axial member 41d connected to the drive shaft of a drive source (not shown).

The applicator 1 is equipped with a controller (not shown) that controls the rotational speed of the discharge roller 3 and the transfer roller 41, on and off switching of the control valve 23 and the cartridge heater, the amount of circulating cooling water, and so forth, to provide sequence control over the operation of the applicator 1 in response to the hot melt adhesive used, the application pattern, and the like.

The sequential operation of the applicator 1 is then described.

A hot melt adhesive is put in a tank (not shown) and melted therein. The discharge roller 32 and the transfer roller 41 rotate at equal peripheral speeds. The nip roller 42 also rotates at the same peripheral speed as the transfer roller 41. The feeding speed of the web S is set equal to the peripheral speed of the transfer roller 41.

The molten hot melt adhesive is fed by means of a pump (not shown) through the feed pipe 21 of the feeding means 2 to the inside of the roller main body 32 of the discharge roller 3.

The hot melt adhesive fed from the feeding means 2 flows in the main conduit 35b and the branched conduits 35c provided in the body 35 of the roller main body 32 and enters the recesses 33 through the respective inlets 34 formed on the outer peripheral surface of the body 35. The hot melt adhesive spreads in each recess 33 along the surface of the surface plate 31, reaches the surface of the discharge roller 3 through the fine pores of the liquid exit parts 3b of the surface plate 31, and exits onto the surface of the transfer roller 41 in a prescribed pattern.

The transfer roller 41 rotates to transfer the hot melt adhesive to the web S emerging from between the transfer roller 41 and the nip roller 42.

In this way, the hot melt adhesive is transferred to a side of the web S (the side of the web S to be coated will hereinafter be referred to as a side 9) to form adhesive (liquid)-coated areas 5 each having substantially the same shape as the plan view shape of the liquid exit part 3b.

In the applicator 1 of the present embodiment, since the liquid exit part 3b is formed of a porous material with a large number of fine pores and provides resistance to the hot melt adhesive passing therethrough, the hot melt adhesive fills the recess 33 relatively uniformly without easily running out on the surface of the surface plate 31. As a result, the hot melt adhesive is forced through the liquid exit part 3b under evenly imposed pressure. Therefore, when the hot melt adhesive is discharged through a plurality of liquid exit parts 3b, the amount of discharged hot melt adhesive varies little from part to part. The amount of the liquid discharged from one exit part 3b also varies little according to the position in that exit part.

The amount of the hot melt adhesive discharged from the surface plate 31 is uniform over the whole discharge area, and the amount of the hot melt adhesive adhered to the transfer roller 41 is also uniform over the total area corresponding to the recess 33. The thus uniformly adhered hot melt adhesive is transferred to the web S. Accordingly, the adhesive-coated area 5 (the area of the web S coated with the hot melt adhesive) formed on the web S has the hot melt adhesive uniformly applied thereto.

As described, when an adhesive is applied to a substrate in a prescribed pattern, the applicator 1 achieves uniform application of the adhesive with no unevenness over the entire area to be coated of the substrate.

Since the shape of the hot melt adhesive exited on the surface of the discharge roller and the resultant shape of the liquid-coated area 5 are decided not by the opening shape of the recess 33 but the shape of the liquid exit part 3b of the surface plate 31, changeover of an application pattern can easily be done by changing the surface plates 31. Since the surface plate 31 of the applicator 1 according to the present embodiment is detachably fixed to the roller main body 32, an adhesive application pattern can be changed simply by the replacement of the surface plate 31. There is no need to change the recess-forming plate 36 or the roller main body 32.

Figure 5:
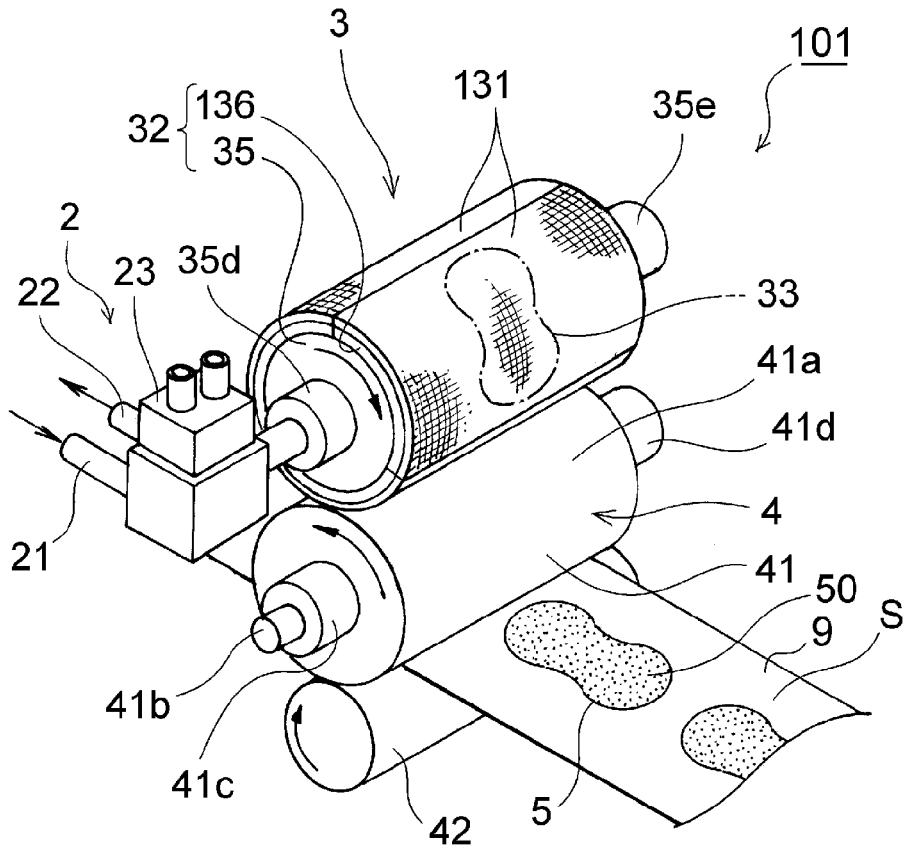
FIG. 5 is a perspective of an essential part of an embodiment of the liquid applicator according to the second aspect of the invention.
Figure 6:
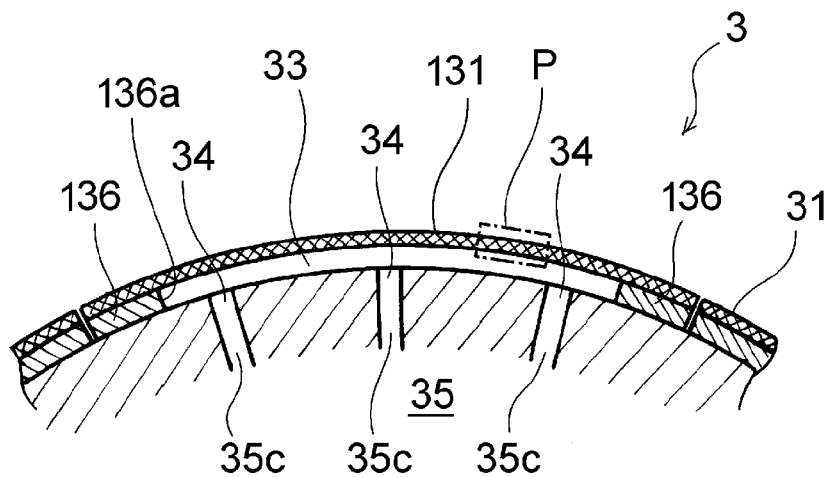
FIG. 6 is a cross-section of an essential part of a discharge roller used in the embodiment of the liquid applicator according to the second aspect of the invention, displaying the structure of the outer periphery of the discharge roller.

An embodiment of the liquid applicator according to the second aspect of the invention will then be described by way of FIGS. 5, 6, and 3.

FIG. 5 is a perspective of an essential part of a liquid applicator 101 as an embodiment of the second aspect of the invention.

The liquid applicator 101 is an apparatus for applying a hot melt adhesive and includes, as illustrated in FIG. 5, feeding means 2 for feeding a hot melt adhesive, a discharge roller 3 that discharges the hot melt adhesive fed from the feeding means 2 in a prescribed pattern, and transfer means 4 for transferring the hot melt adhesive 50 discharged from the discharger roller 3 in a prescribed pattern to a continuously moving web (substrate) S. The numeral 5 in FIG. 5 indicates an area coated with the hot melt adhesive 50 of the web S (adhesive-coated area).

The feeding means 2 has a tank (not shown) storing a hot melt adhesive, a feed pipe 21 connecting the tank and the discharge roller 3, a pump (not shown) fitted in the feed pipe 21, a return pipe 22 branched from the feed pipe 21, and a control valve 23 switching the hot melt adhesive flow from the feed pipe 21 between the return pipe 22 and the discharge roller 3.

As illustrated in FIGS. 5 and 6, the discharge roller 3 includes a surface plate 131 forming the outer peripheral portion of the discharge roller 3 and a roller main body 32 constructing the portion radially inward of the surface plate 131 (the portion proximal to the rotational axis).

The roller main body 32 has a columnar shape with a plurality of recesses 33 arranged at intervals in the circumferential direction. Each of the recesses 33 is formed by providing a level difference from the other portion. The bottom of the recess 33 is provided with inlets 34 for introducing a hot melt adhesive into the recess 33. The surface plate 131 is fixed to the outer peripheral surface of the roller main body 32 to cover the recess 33.

As illustrated in FIGS. 6 and 3, the roller main body 32 of the applicator 101 includes a body 35 constituting the part of the roller main body 32 close to the rotational axis and pattern plates 136. The pattern plate 136 has an opening 136a of prescribed shape. The inner wall of the opening 136a forms the recess 33. The body 35 has a columnar shape with the inlets 34 formed on its outer peripheral surface. The pattern plate 136 is structurally similar to the recess-forming plate in the applicator 1.

The pattern plates 136 are fixed in a configuration that the inlets 34 may be located within the openings 136a.

The pattern plates 136 are fixed to the outer periphery of the body 35 in series in the peripheral direction of the body 35. Thus, the pattern plates 136 form the outer peripheral portion of the cylindrical roller main body 32. The surface plate 131 is fixed on the further radially outer side of the peripheral portion, formed of the pattern plates 136, of the roller main body. The surface plate 131 is fixed at a position such that the recess 33 formed by the opening 136a of the pattern plate 136 is totally covered therewith. Fixing the pattern plate 136 to the surface plate 131 may precede fixing to the body 35. Similarly to the pattern plates 136, the surface plates 131 are arranged in the peripheral direction of the body 35, one on each pattern plate 136. Otherwise, the surface plate 131 may have a length extending the whole periphery of the roller main body 32, in which case, the outer peripheral surface of the discharge roller 3 is formed of a single surface plate 131.

As illustrated in FIG. 3, the roller main body 32 has in its core a main conduit 35b extending in the rotation axial direction of the discharge roller 3, through which a hot melt adhesive fed from the feed pipe 21 flows. The roller main body 32 also has inside branched conduits 35c interconnecting the main conduit 35b and the inlets 34. In the discharge roller 3 of the applicator 101, too, a hot melt adhesive fed through the feed pipe 21 of the feeding means 2 flows through the main conduit 35b and the branched conduits 35c and enters the recess 33 through the inlets 34. The hot melt adhesive spreads in the recess 33 in directions along the surface of the surface plate 131 (almost parallel to the plane of the surface plate 131) and then exits through the pores of the surface plate 131 out of the surface of the discharge roller 3. The directions along the surface of the surface plate 131 can be said to be directions perpendicular to the depth direction of the recess 33. The phrase "spread in directions along the surface of the surface plate 131" means to spread in at least said directions and is not intended to exclude spreading in a direction perpendicular to the surface of the surface plate 131 (i.e., the depth direction of the recess) simultaneously with the spread in said directions.

Figure 7:
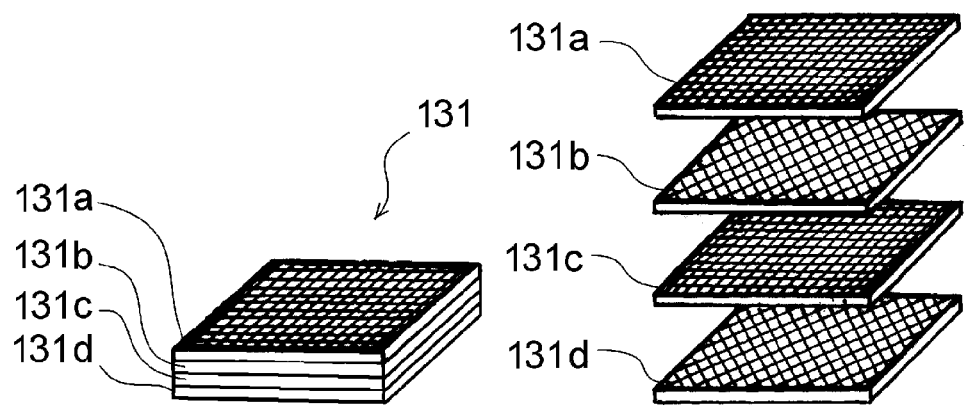
FIG. 7 illustrates the structure of a surface plate used in the embodiment of the liquid applicator according to the second aspect of the invention.

The surface plate 131 used in the applicator 101 is a stack of a plurality of porous materials 131a, 131b, 131c, and 131d as shown in FIG. 7. A part of the surface plate 131, e.g., the part indicated by symbol P shown in FIG. 6 is illustrated in FIG. 7.

The porous materials that can be used in the second aspect of the invention are preferably, but are not limited to, those having numerous through-pores interconnecting both sides thereof regularly arranged in the planar directions (directions perpendicular to the thickness direction). Those having pores irregularly arranged in the planar directions are also employable. Examples of porous materials that are preferably used in the present invention, particularly in the second aspect of the invention include a metal mesh, an etched porous material, punching metal, sintered metal, and ceramic. The plurality of porous materials may be a combination of porous materials of the same or different kinds.

In using punching metal or an etched porous material as the porous material forming the surface plate 131, the opening area ratio (ratio of the total area of the pores) is preferably 1% to 76%, more preferably 10% to 60%. The number of the pores per $cm^2$ of the porous material is preferably about 1 to 10,000, more preferably about 125 to 2,500. The size of the individual pores is preferably 0.05 to 2 mm.

In using a metal mesh, sintered metal or ceramics as the porous material forming the surface plate 131, the opening area ratio (the total area of the pores) is preferably 1% to 80%, more preferably 10% to 60%. The area of the individual pores is preferably 0.002 to 3.2 $mm^2$, more preferably 0.004 to 0.5 $mm^2$.

The average pore size and pore area of the porous material are measured as follows. The porous material is observed from right above with an optical microscope to measure the area S of at least 10 openings as observed on the surface. The measured values are substituted for S in expression: $S=\pi/4 \times d^2$ ($\pi=3.14$) to calculate d's, which are averaged to give a circular equivalent diameter. The pore area is easily measured by encircling an arbitrarily chosen dot on the image as observed using, for example, a digital HD microscope VH-7000 from Keyence.

Figure 8:
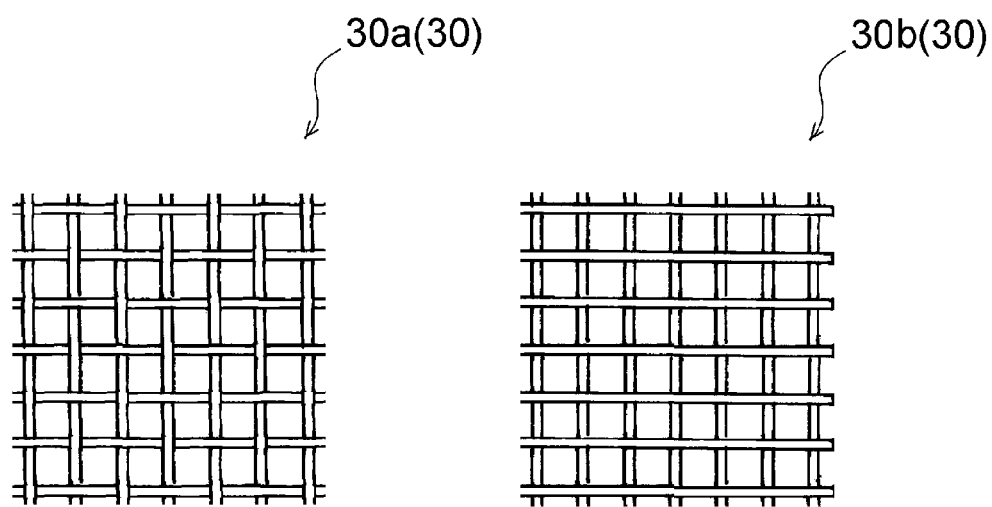
FIG. 8 is a fragmentary, enlarged plan showing preferred examples of a metal mesh used as a porous material.

FIG. 8 shows metal meshes that can be used preferably as the porous material.

Each metal mesh 30 shown in FIG. 8 is made of a plurality of warp wire filaments intersected by a plurality of woof wire filaments forming a grid of square pores regularly arranged in two perpendicularly crossing directions.

The metal mesh 30a, one of the metal meshes 30, is a plain-woven metal mesh made of the warp wire filaments and the woof wire filaments. The plain-woven warp wire filaments and the woof wire filaments may or may not be bonded at their intersections by fusion or a like bonding means. The metal mesh 30b, the other of the metal meshes 30 of FIG. 8, a plurality of woof wire filaments are superposed on a plurality of warp wire filaments with their intersections fusion bonded.

Figure 9A:
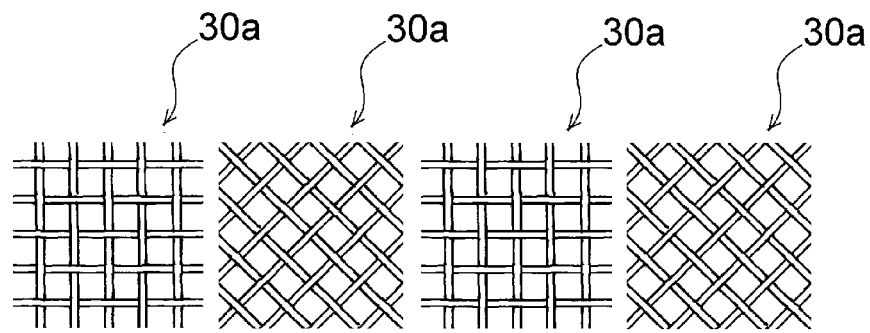
FIG. 9(a), FIG. 9(b), and FIG. 9(c) provide preferred examples of a combination of porous materials and a way of superposing the porous materials.
Figure 9B:
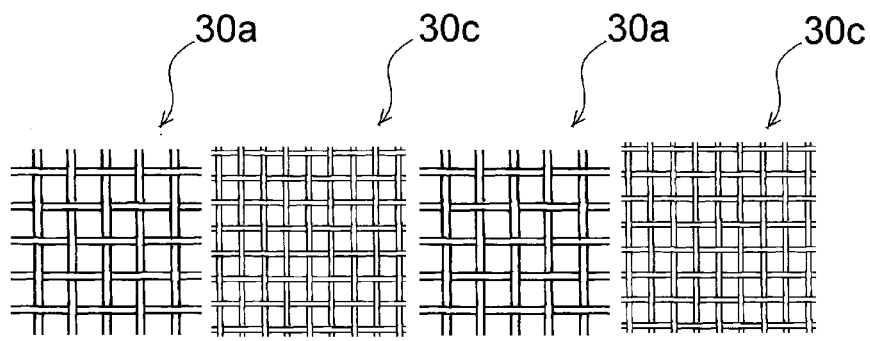
Figure 9C:
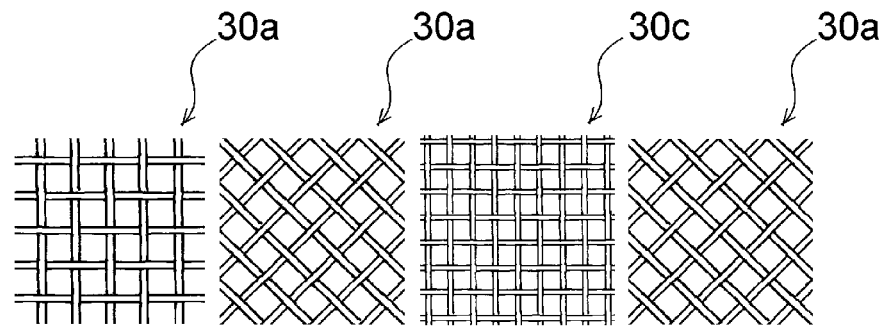

FIGS. 9(a) through 9(c) and 10 each illustrate a preferred example of a combination of porous materials and a way of superposing the porous materials. The leftmost of the four metal meshes (porous materials) shown in each of FIGS. 9(a) to 9(c) is the outermost of the metal meshes constructing the surface plate in the radial direction of the discharge roller 3. The other three metal meshes are successively superposed beneath the leftmost one in left to right order. The rightmost metal mesh (porous material) comes to the innermost in the radial direction of the discharge roller 3 (the most proximal to the rotational axis).

In the example of FIG. 9(a), four metal meshes 30a (porous materials) of a kind (having the same pore shape and size) are laminated at a crossing angle increasing by 45°.

In the example of FIG. 9(b), two kinds of metal meshes (porous materials) 30a and 30c different in pore size alternate in the thickness direction to make a stack of four metal meshes.

In the example of FIG. 9(c), three metal meshes (porous materials) 30a having the same pore shape and size and one metal mesh (porous material) 30c equal to the other three in pore shape but different in pore size are stacked.

Figure 10:
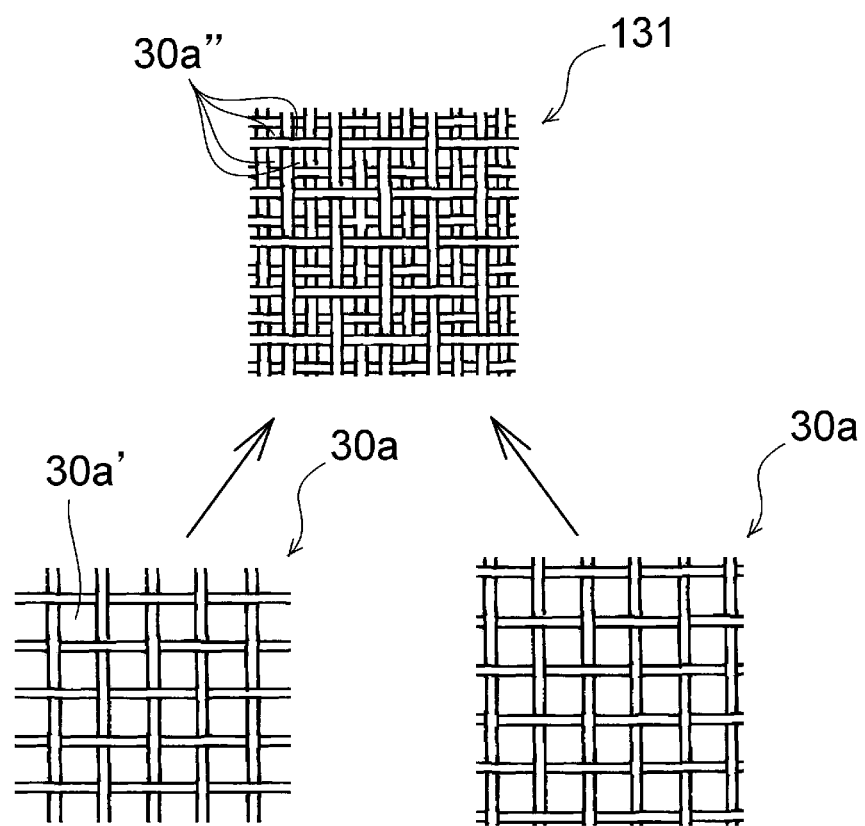
FIG. 10 provides a preferred example of a combination of porous materials and a way of superposing the porous materials.

In the example of FIG. 10, two metal meshes 30a,30a of a kind having the same pore shape and size are superposed on each other with their pores out of alignment.

The surface plate used in the invention is preferably a stack of a plurality of porous materials at least two of which form a crossing angle as in the examples of FIGS. 9(a) and 9(c).

The number of the porous materials such as metal meshes to be combined at a crossing angle of 45° is not limited to four and may be two or three or five to ten. The crossing angle between the adjoining metal meshes is not limited to 45° and may be 30° or 60°. The stack may contain adjoining porous materials superposed at no crossing angle and adjoining porous materials superposed at a crossing angle.

As used herein the phrase "at a crossing angle" means that, in the case of metal meshes having warp and woof, the warp direction of a metal mesh is coincide with neither the warp direction nor the woof direction of another metal mesh.

A stack of porous materials at least two of which are different in pore size as in the examples of FIGS. 9(b) and 9(c) is also a preferred surface plate for use in the invention. Three or more metal meshes having different pore sizes may be used in combination.

A stack of porous materials at least two of which have their pores out of alignment as in the example of FIG. 10 is also a preferred surface plate 131 for use in the invention. It is more preferred that at least two of the porous materials be superposed on each other in a fashion that, as with the case of the surface plate 131 of FIG. 10, a pore 30a' of one of the porous materials is divided into a plurality of sections 30a",30a", . . . by a part other than the pores of the other porous material (namely, the wire filament in the case of a metal mesh) extending across the pore 30a'.

While the surface plate used in the second aspect of the invention is a stack of two or more porous materials such as metal meshes, the adjoining porous materials may or may not be bonded to each other. Where necessary, the adjoining porous materials are bonded by sintering, fusion (e.g., welding), adhesive application, or like means.

The surface plate 131 used in the applicator 101 is detachably fixed to each of the pattern plates 136 with a fastener such as a bolt. The stack of the porous materials constructing each surface plate 131 is united simultaneously with the fixing of the surface plate 131 to the pattern plate 136. The stack of the porous materials constructing the surface plate 131 may previously be united by uniting means such as a bolt or a clamp before they are fixed to the roller main body 32.

Each of the pattern plates 136 is also detachably fixed to the body 35 with a fastener such as a bolt. The fastener for fixing the pattern plate 136 to the body 35 may double as a fastener for fixing the surface plate 131 to the pattern plate 136.

The surface plate 131 used in the applicator 101 has a stacked structure of a plurality of porous materials in every planar direction thereof (directions perpendicular to the thickness direction). Therefore, a hot melt adhesive is discharged from all the area of the portion of the surface plate 131 that covers the recess 33, the shape of the discharged hot melt adhesive being substantially equal to the opening shape of the recess 33.

In the present embodiment, the recess 33 has a constant depth (equal to the distance between the bottom 35a of the recess 33 and the surface plate 131) over the entire area thereof. The depth of the recess 33 is preferably 0.1 to 5.0 mm, more preferably 0.5 to 3.0 mm.

The number of the inlets 34 to be provided in the recess 33 is preferably one per 0.5 to 10 cm$^2$ of the bottom area of the recess 33.

The overall thickness of the surface plate 131 is preferably 2 mm or less, more preferably 1 mm or less, even more preferably 0.3 to 0.9 mm, to secure even application over the entire area to be coated of a substrate. For the same viewpoint, the overall thickness of the surface plate 131 is preferably 0.05 to 20 times, more preferably 0.1 to 2 times, the depth of the recess 33.

The body 35 of the roller main body 32 has, at one axial end thereof, a tubular member 35d rotatably connected to the end of the feed pipe 21 of the feeding means 2 and, at the other end, an axial member 35e connected to a drive shaft of a drive source (not shown). The body 35 of the roller main body 32 has a heater (not shown) such as a cartridge heater inside of it, whereby the temperature inside the roller main body 32 is adjusted to control the viscosity of the hot melt adhesive flowing there.

The transfer means 4 includes a transfer roller 41 that rotates in contact with the outer peripheral surface, which is formed of the surface plate 131, of the discharge roller 3 and the web S, and a nip roller 42 that is placed beneath the transfer roller 41, between which the web S is moved.

The transfer roller 41 has its peripheral surface 41a lines with a release material such as silicone rubber so that the discharged hot melt adhesive may easily be released and transferred onto the substrate. The transfer roller 41 has inside thereof a conduit line (not shown) so that cooling water is circulated through a water conduit 41b to maintain the transfer roller 41 at low temperatures. The transfer roller 41 has at one axial end thereof a tubular member 41c rotatably connected to the water conduit 41b and, at the other end, an axial member 41d connected to the drive shaft of a drive source (not shown).

The applicator 101 is equipped with a controller (not shown) that controls the rotational speed of the discharge roller 3 and the transfer roller 41, on and off switching of the control valve 23 and the cartridge heater, the amount of circulating cooling water, and so forth, to provide sequence control over the operation of the applicator 101 in response to the hot melt adhesive used, the application pattern, and the like.

The sequential operation of the applicator 101 is then described.

A hot melt adhesive is put in a tank (not shown) and melted therein. The discharge roller 32 and the transfer roller 41 rotate at equal speeds. The nip roller 42 also rotates at the same peripheral speed as the transfer roller 41. The feeding speed of the web S is set at the peripheral speed of the transfer roller 41.

The molten hot melt adhesive is fed by means of a pump (not shown) through the feed pipe 21 of the feeding means 2 to the inside of the roller main body 32 of the discharge roller 3.

The hot melt adhesive fed from the feeding means 2 flows in the main conduit 35b and the branched conduits 35c provided in the body 35 of the roller main body 32 and enters the recesses 33 through the inlets 34 formed on the outer peripheral surface of the roller main body 32. The hot melt adhesive spreads in each recess 33 along the surface of the surface plate 131, reaches the surface of the discharge roller 3 through the pores of the surface plate 131 formed of combined porous materials, and exits onto the surface of the transfer roller 41 in a prescribed pattern.

The transfer roller 41 rotates to transfer the hot melt adhesive to the web S emerging from between the transfer roller 41 and the nip roller 42.

In this way, the hot melt adhesive is applied to the surface of the web S (the side 9). An adhesive (liquid)-coated area 5 having substantially the same shape as the opening shape of the recess 33 is thus provided on the surface of the web S.

According to the application 101 of the present embodiment, since the surface plate 131 formed of a stack of porous materials is used, the adhesive exits through a large number of fine pores resulting from combining porous materials. Unevenness of the ease of passage of the adhesive hardly occurs. Therefore, the adhesive can be applied uniformly.

Since the surface plate 131 are made by combining a plurality of porous materials, the porous materials used to make the surface plate 131 or the manner of superposing the porous materials can be varied in accordance with the viscosity or amount of the adhesive discharged from the discharge roller so that the adhesive may be applied under appropriate conditions.

In the applicator 101 of the present embodiment, the entire area of the portion of the surface plate 131 that covers the recess 33 has a stack structure of a plurality of porous materials, and the hot melt adhesive is discharged from the whole area of that portion. Therefore, the spread of the adhesive in the recess 33 is less disrupted or becomes less uneven as compared with the case of using a surface plate with holes distributed in a pattern different from the opening shape of the recess 33 as in the embodiment graphically illustrated in patent document 2. The applicator 101 thus enables applying the adhesive more evenly.

The adhesive that can be used in the first and second aspects of the present invention is preferably a hot melt adhesive.

Adhesives other than a hot melt adhesive are also used, including low-density polyethylene, polyvinyl acetate, silicone resins, and starch.

Examples of the hot melt adhesive include, but are not limited to, styrene rubbers, e.g., a styrene-butadiene-styrene block copolymer (SBS) and a styrene-ethylene-butylene-styrene block copolymer (SEBS); and olefin polymers, e.g., amorphous poly($\alpha$-olefins) (APAO) and an ethylene-vinyl acetate copolymer (EVA).

Examples of the substrate that can be used in the invention include, but are not limited to, sheet materials such as nonwoven fabrics, woven fabrics, resin films, and knitted fabrics; laminate sheets composed of two or more of these sheet materials; and composites composed of the sheet material or laminate sheet further laminated with other member or having other member interposed therein. The substrate may be a continuously fed web or cut lengths fed at a prescribed interval.

The above illustrated applicators are suited to the manufacture of absorbent articles having a pressure-sensitive adhesive layer of a hot melt adhesive and being designed to be attached to a garment via the adhesive layer. Examples of such absorbent articles include those used to absorb body exudates, such as sanitary napkins, panty liners, and incontinence pads. An absorbent article of this type generally includes a liquid retentive topsheet, a sparingly liquid permeable (meant to include liquid impermeable) backsheet, and an absorbent member interposed between these sheets. It has a pressure-sensitive adhesive layer of a hot melt adhesive on its garment contacting side or has a wing on both lateral sides of its oblong main body with a pressure-sensitive adhesive layer of a hot melt adhesive on the garment contacting side of each wing. The adhesive layer can be provided on both the main body and the wings.

In the manufacture of this type of absorbent articles, a hot melt adhesive can be applied by use of the above described applicators to form a pressure-sensitive adhesive layer having a prescribed shape. The substrate is a continuous web of a sheet material defining the garment contacting side, a continuous web of the sheet material having other member(s) superposed thereon, or cut lengths of the sheet material having other member(s) superposed thereon. The absorbent articles are produced in otherwise the same manner as conventional products.

While the first and second aspects of the present invention have been described with reference to certain preferred embodiments, the invention is not deemed to be limited thereto, and changes and modifications can be made therein as exemplified as follows.

Figure 11:
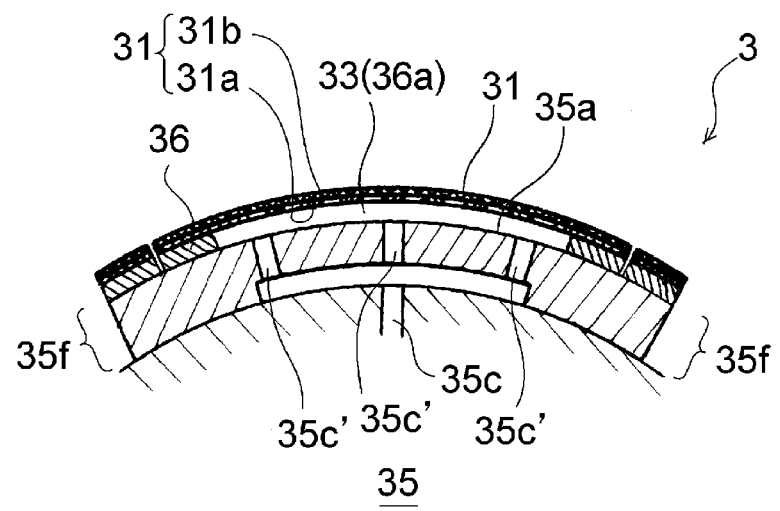
FIG. 11 illustrates another embodiment of the liquid applicator according to the invention (equivalent to FIG. 2).

As illustrated in FIG. 11, the outer peripheral portion 35f of the body 35 of the discharge roller 3, the portion from the outer peripheral surface 36a of the body 35 to a prescribed depth, may be a separate member that is detachably fitted over the other radially inward portion of the body 35. The member providing the outer peripheral portion 35f has a manifold structure for branching one branched conduit 35c into a plurality of branched conduits 35e',35c',35c'. Such a structure further facilitates flow designing for leading an adhesive to the recess 33.

The flow path for leading a hot melt adhesive fed from the feeding means 2 to the recess 33 is not restricted and may be varied as long as an adhesive is introduced into the recess 33.

Figure 12:
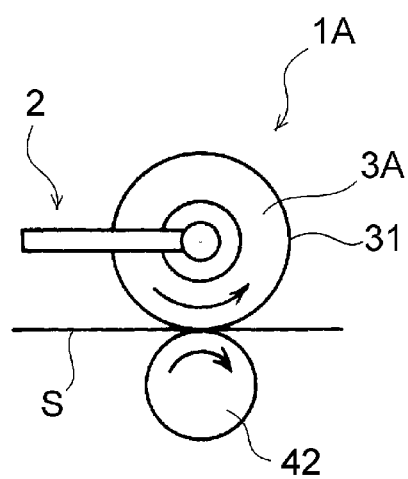
FIG. 12 is a schematic side view illustrating still another embodiment of the liquid applicator according to the invention.

FIG. 12 illustrates an adhesive applicator 1A having a discharge roller 3A which has the same structure as the discharge roller 3 shown in FIG. 1 except for being driven by the nip roller 42. The adhesive applicator 1A does not have the transfer roller 41. The adhesive applicator 1A applies a hot melt adhesive from the outer surface of the discharge roller 3A directly onto a web S emerging from between the discharge roller 3A and the nip roller 42. In the adhesive applicator 1A, too, the outer surface of the discharge roller 3A is formed by a surface plate 31. The surface plate 31 has, in its portion covering the underlying recess, a liquid exit part and a liquid block part. The liquid exit part is formed of a porous material with a large number of fine pores and permits a hot melt adhesive to be forced out therethrough. Accordingly, the applicator 1A has the same effects as the application 1.

The adhesive applicator according to the second aspect of the invention may also dispense with the transfer roller.

Figure 13:
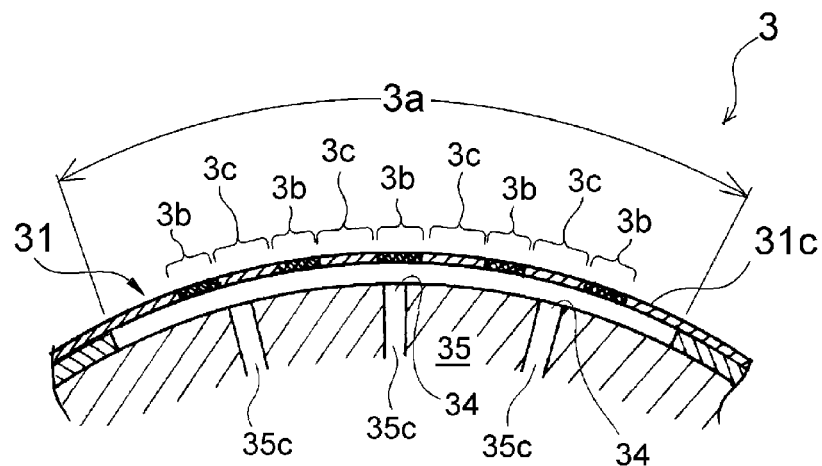
FIG. 13 illustrates still another embodiment of the liquid applicator according to the invention (equivalent to FIG. 2).

The surface plate 31 used in the applicator 1, which is a joined stack of the pattern plate 31a and a porous plate 31b, may be replaced with a surface plate 31 formed of a porous plate 31c having part of its fine pores subjected to a filling treatment to form a liquid block part 3c as illustrated in FIG. 13. The filling treatment is filling fine pores of a porous material with a filler such as a resin or a metal to block passage of a liquid. A filler is preferably forced into the pores in a molten state and then solidified.

In the embodiment shown in FIG. 13, the liquid block part 3c formed by the filling treatment and the liquid exit part 3b without the filling treatment is formed in a portion 3a which covers the recess 33 of the porous plate 31c, and the effect similar to the applicator 1 mentioned above is exhibited.

Furthermore, the surface plate 31 used in the applicator 1, with the pattern plate 31a inside and the porous plate 31b outside, may have the porous plate 31b inside and the pattern plate 31a outside. A three-layered surface plate having a pair of porous plates and a pattern plate therebetween is also usable. The porous plate may be composed of a plurality of layers.

Figure 14:
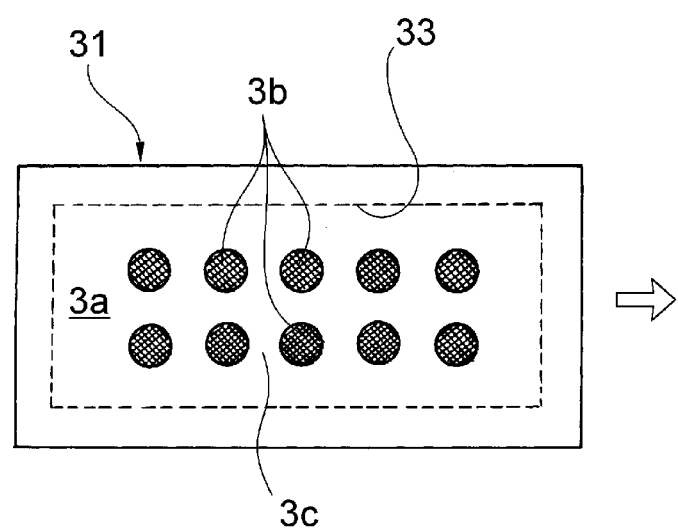
FIG. 14 illustrates liquid exit parts and a recess in still another embodiment of the liquid applicator according to the invention.

The recess 33 may have any opening shape. The opening shape may be, for example, an oblong rectangle as shown in FIG. 14 as well as the eye mask shape shown in FIG. 1. The opening shape may also be a square, a circle, an elongated circle, a diamond, and a heart, and so on. The hole 31a' and the liquid exit part 3b may have any shape, the shape thereof being not limited to a rectangle with the longitudinal direction coincide with the axial direction of the discharge roller. For example, the shape thereof may be a rectangle with the longitudinal direction coinciding with the peripheral direction of the discharge roller, a circle as in FIG. 14, a square, an elongated circle, a diamond, a heart, and so forth. A combination of differently shaped liquid exit parts 3b may be provided for one recess 33.

The number of the liquid exit parts 3b to be formed per recess 33 is one or more than one. When more than one liquid exit parts 3b are to be formed, the number is, for example, 2 to 1000. The number is preferably 2 to about 100. The number of the liquid exit parts 3b may vary from recess 33 to recess 33.

The adhesive applicator according to the second aspect of the invention may be modified such that an adhesive discharged from the discharge roller 3 is directly applied to a substrate without using transfer means like the adhesive applicator 1A shown in FIG. 12. In this ease, too, the entire area of the portion of the surface plate (constructing the outer surface of the discharge roller 3A) that covers the underlying recess is formed of porous materials, and a hot melt adhesive is discharged from the whole area of that portion. Therefore, the same effects as by the applicator 101 can be produced.

The surface plate 131 used in the applicator 101 which has pores all over the planar directions (the directions perpendicular to the thickness direction) may be replaced with a surface plate having other than the portion covering the recesses 33 masked with a masking material such as silicone, an epoxy resin, or a solder. In this case, the masking shape of the surface plate is preferably such that the masking edge is on the extension line starting from the center of the discharge roller and passing the edge of the recess. The masking edge may coincide with the edge of the recess.

FIG. 15(a) represents an example in which the surface plate is masked in other than the portion covering the recess 33. FIGS. 15(b) through 15(d) display examples in which the surface plate is masked in not only other than the portion covering the recess 33 but a part of the portion covering the recess 33. By using the surface plate 131 of FIGS. 15(b) to 15(d), a hot melt adhesive is applied in the same shape as the unmasked portion. In FIGS. 15(a) through 15(d) the reference numeral 131e indicates a masked portion.

Masking with a masking material may be filling the pores of only the outermost of the plurality of porous materials making up the surface plate or of two or more or all of the porous materials making the surface plate. From the standpoint of securing stability in continuous application by making the surface of the surface plate uniform with little level difference, it is preferred that masking with a masking material be applied not to the outermost porous material but to any other porous material.

A surface plate 131 having a masked portion and an unmasked portion surrounded by the masked portion may be used in a manner such that the adhesive fed by the feeding means 2 is led directly to the unmasked portion without using the recess 33. The unmasked portion described above and the flow path leading an adhesive to the recesses 33 in the aforementioned embodiments are not particularly limited and may be changed variously.

Part of the surface plate being so masked or blocked, the adhesive is forced through the unmasked open-pore portion at an increased rate, resulting in a clearer application pattern. Furthermore, use of partly masked surface plate makes it feasible to apply an adhesive at even a reduced amount, achieving efficient application.

Figure 16A:
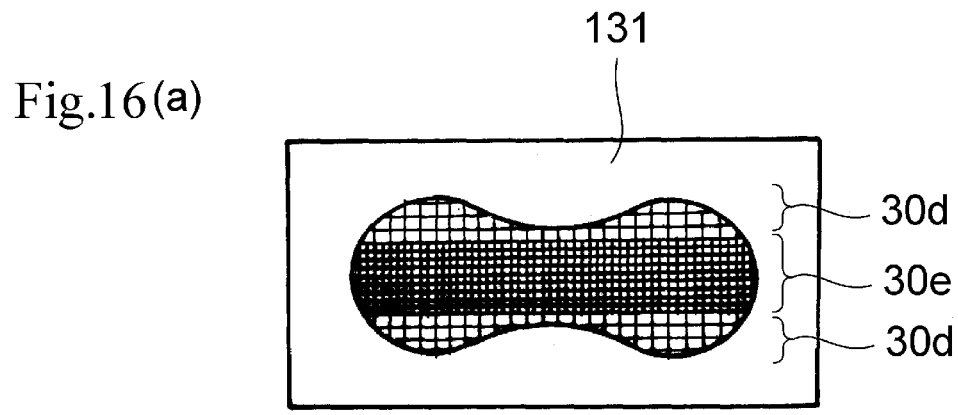
FIG. 16(a) is a plan of a surface plate used in still another embodiment of the liquid applicator according to the second aspect of the invention.
Figure 16B:
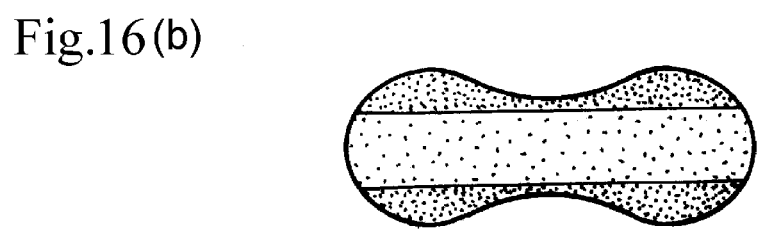
FIG. 16(b) is a plan of the adhesive applied in this embodiment.

The surface plate may be designed to have two regions intentionally varied in pore size so as to make a difference in amount of discharge. The surface plate 131 illustrated in FIG. 16(a) has two regions 30d and 30e different in pore size provided in the radially outermost porous material so that the amount of an adhesive discharged differs between the regions 30d and 30e, which results in making a difference in the amount of the adhesive applied to a substrate (see FIG. 16(b)). In this embodiment, too, the adhesive is discharged evenly in the individual regions.

The recess 33 may have any opening shape. The outline of the recess 33 may be made solely of straight lines or curved lines or made of a combination of straight lines and curved lines. The pores of the individual porous materials may have any shape in addition to a square shape. Examples of the opening shapes of the recesses and the openings include circular, elongated circular, heart-shaped, eye mask-shaped, elongated circular with the middle narrowed, rectangular, triangular, and rhombic.

The liquid applicator according to the first and second aspects of the invention is used to apply not only an adhesive but a liquid other than an adhesive. Examples of the liquid that can be applied include oils, emulsions, creams, humectants, and lotions.

In the manufacture of absorbent articles, the liquid applicator according to the present invention is preferably used as well to apply an adhesive to a component constructing an absorbent article. A component with the applied adhesive is joined to other component on its adhesive side. Examples of the component of an absorbent article include, but are not limited to, a topsheet, an absorbent member, a backsheet, a wing-forming sheet, and a standing cuff-forming sheet.

In the description given above, particulars of a certain embodiment that have been omitted to avoid redundancy can appropriately be complemented by the corresponding description of other embodiments. Particulars described as being characteristic of a certain embodiment can apply to other embodiments appropriately. Particulars of the individual embodiments are appropriately interchangeable between embodiments.

EXAMPLES

The present invention will now be illustrated in greater detail by of Examples, but it should be understood that the invention is not construed as being limited thereto.

Example 1

An adhesive was applied to a web of release paper having a basis weight of 38 g/m$^2$ by the use of the liquid applicator illustrated in FIG. 1, and the applied adhesive was evaluated.

Each of the surface plates of the discharge roller was a multilayer stainless steel mesh made as follows. Four stainless steel meshes each having mesh size #100 (mesh pore size: 0.16 mm×0.16 mm; 100 pores per 25.4 mm) and a thickness of 0.15 mm were used as porous materials. The four meshes were superposed one on top of another at a crossing angle increasing by 45 degrees for every superposition. A pattern plate formed of a 0.15 mm stainless steel plate was superposed on the resulting stack of meshes, and another stainless steel mesh of the kind described above was superposed on the pattern plate. The stack of six layers was united by sintering to give the surface plate having an overall thickness of 0.9 mm. The resulting surface plate had the lonely stainless steel mesh as an outermost layer, the pattern plate next to the outermost layer, and the stack of the four stainless steel meshes (specifically the undermost layer of the stack) to be in contact with the recess-forming plate described below. The pattern plate had holes 31a', through which a liquid was to pass, arranged in a pattern corresponding to the adhesive areas (liquid-coated areas 5) shown in FIG. 17.

Figure 18:
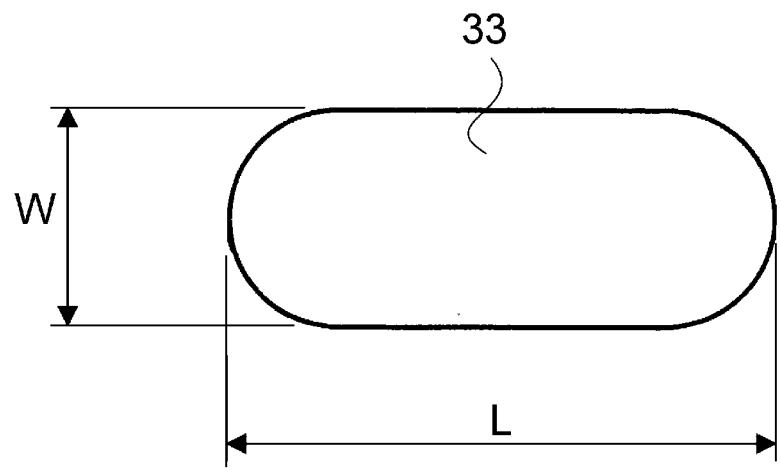
FIG. 18 illustrates the shape of the recess in Examples 1 and 2.

Each recess-forming plate 36 which was a 1.0 mm thick stainless steel plate having a hole 36a was fixed to the roll body 35 with bolts together with each of the surface plates 31. The hole 36a of the recess-forming plate 36 had an elongated elliptic shape of 47 mm in width (W), 132 mm in length (L), and 57.3 cm$^2$ in area. The inner circumferential wall of the hole 36a of the recess-forming plate 36 and the outer peripheral surface of the body 35 defined a 1.0 mm deep recess 33 having the shape shown in FIG. 18.

The discharge roller of the liquid applicator was set at 165° C. The adhesive was fed at a velocity of 100 m/min under a liquid pressure of 1 Mpa. A styrene rubber hot melt adhesive, a styrene-ethylene-butylene-styrene block copolymer (SEBS), was used at a viscosity of 1600 mPa·s (at 160° C.).

Figure 17:
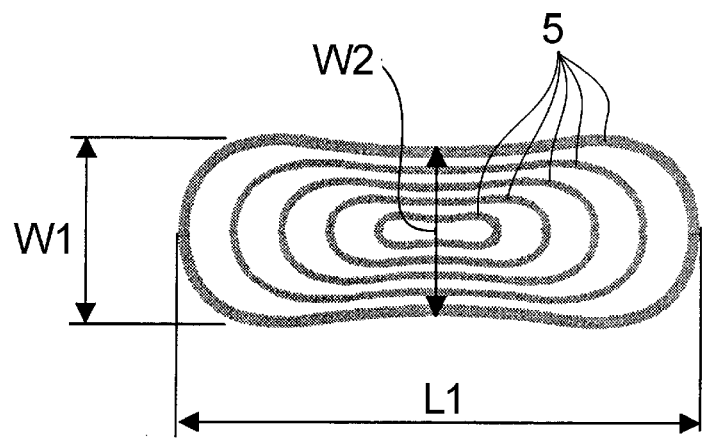
FIG. 17 shows the pattern of the adhesive applied in Examples 1 and 2.

The application pattern of the adhesive (liquid-coated areas 5) was as shown in FIG. 17. The holes 31a' of the pattern plate had the same pattern. The application pattern of the adhesive as designed had a total area of 21.3 cm$^2$, the dimension (the maximum size) of 130 mm (length L1) by 48 mm (width W1), the minimum width (at the narrowed, middle portion) of 42 mm (width W2), and a basis weight of 50 g/m$^2$.

Example 2

An adhesive was applied to release paper in the same manner as in Example 1, except for changing the structure of the surface plate 31 as follows, and the applied adhesive was evaluated.

The same four stainless steel meshes as used in Example 1 were stacked, and the stack was superposed on the same pattern plate 31a as used in Example 1. The stack of five layers was united by sintering to give a surface plate having an overall thickness of 0.75 mm. The surface plate was used with the stack of four stainless steel meshes outside and the pattern plate 31a facing the recess-forming plate 36.

Example 3

An adhesive was applied to release paper having a basis weight of 38 g/m² by the use of the liquid applicator illustrated in FIG. 5, and the applied adhesive was evaluated.

Each of the surface plates 131 of the discharge roller was a multilayer stainless steel mesh made as follows. Four stainless steel meshes each having mesh size #100 (mesh pore size: 0.16 mm×0.16 mm; 100 pores per 25.4 mm) and a thickness of 0.15 mm were superposed one on top of another at a crossing angle increasing by 45 degrees for every superposition as illustrated in FIG. 9(a). The superposed four metal meshes were united by sintering and with an adhesive to make a surface plate with an overall thickness of 0.6 mm. Of the metal meshes used to make the surface plate, the next to the outermost metal mesh had been masked with an epoxy resin in its region surrounding an adhesive application pattern (adhesive-coated area 5) shown in FIG. 19 prior to the superposition.

Figure 19:
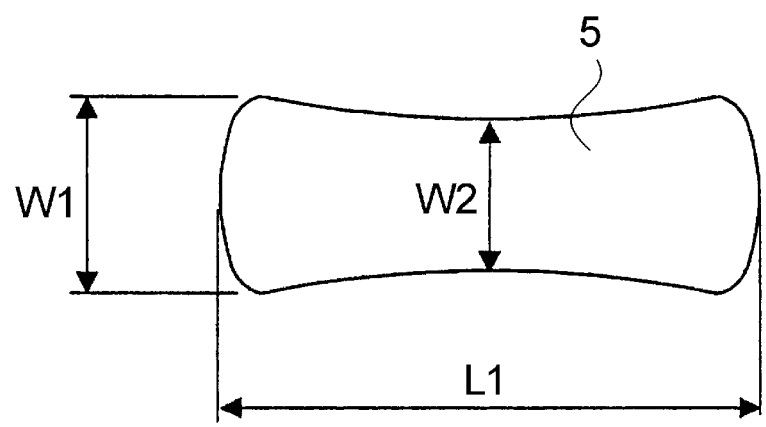
FIG. 19 illustrates the pattern of the adhesive applied in Examples 3 to 5 and Comparative Example 1.

A 1.0 mm thick, stainless steel pattern plate 136 having an opening 136a of the same shape as the adhesive-coated area 5 of FIG. 19 was fixed to the body 35 together with the surface plate 131 with bolts. The opening 136a of the pattern plate had the shape of an elongated circle with the middle narrowed, a width of 48 mm, a length of 130 mm, and an area of 52.4 cm². The inner circumferential wall of the opening of the pattern plate and the outer peripheral surface of the body 35 defined a recess 33 having the shape of FIG. 19. As viewed from a direction normal to the periphery of the discharge roller, the size and shape of the recess were equal to those of the adhesive-coated area 5 shown in FIG. 19.

The temperature of the discharge roller of the liquid applicator was set at 165° C. The adhesive was fed at a velocity of 100 m/min under a liquid pressure of 1 Mpa. A styrene rubber hot melt adhesive, a styrene-ethylene-butylene-styrene block copolymer (SEBS), was used at a viscosity of 1600 mPa·s (at 160° C.).

The application pattern of the adhesive was as shown in FIG. 19. The recess and the masking portion also had the same shape as that of FIG. 19. The application pattern of the adhesive as designed had an area of 52.4 cm², the dimension (maximum size) of 130 mm (length L1) by 48 mm (width W1), the minimum width (at the narrowed, middle portion) of 37 mm (width W2), and a basis weight of 30 g/m².

Example 4

An adhesive was applied to release paper in the same manner as in Example 3, except for changing the structure of the surface plate 131 as follows, and the applied adhesive was evaluated.

The same four stainless steel meshes as used in Example 3 were stacked and united in the same manner as in Example 3, except that the masking was applied to the metal mesh that was to form the outermost peripheral surface of the surface plate.

Example 5

An adhesive was applied to release paper in the same manner as in Example 3, except for changing the structure of the surface plate 131 as follows, and the applied adhesive was evaluated.

The same four stainless steel meshes as used in Example 3 were stacked and united in the same manner as in Example 3, except that the masking was applied to none of the meshes.

Comparative Example 1

An adhesive was applied to release paper in the same manner as in Example 1, except that metal plates having the structure described below were disposed around the peripheral surface of the roller main body in place of the surface plates and the recess-forming plates of Example 1. The applied adhesive was evaluated. In Comparative Example 1, the pattern of the adhesive-coated area 5 shown in FIG. 19 was adopted. That is, the adhesive was applied in the same pattern as in Example 3.

The metal plate had a thickness of 12 mm and a 7 mm deep recess of the shape shown in FIG. 19. The metal plate had a porous material of sintered metal having a diameter of 350 μm disposed in the recess. The liquid passage diameter of the porous material was 40 μm. The recess of the metal plate had a large number of openings at its bottom interconnected to branched conduits for introducing an adhesive into the recess. All the portion filled with the porous material served as a liquid exit part.

The application pattern as designed has an area of 52.4 cm², the dimension (maximum size) of 130 mm by 48 mm, the minimum width (at the narrowed middle portion) of 37 mm, and a basis weight of 30 g/m².

Method and Results of Evaluation:

The adhesive applied to release paper by the use of the apparatus of Examples 1 to 5 and Comparative Example 1 was evaluated as follows. The evaluation was carried out in quintuplicate (n=5).

(1) Dimension

The adhesive-coated area on release paper was measured in length (L1) and width (W2) at the narrowed middle portion. The measured values were divided by the respective designed values to calculate a dimensional ratio of the measured value to the designed value. Ratios up to 110% relative to the designed value were regarded acceptable.

(2) Variation of Amount of Applied Adhesive and Evaluation of Uniformity

The applied adhesive are (n=5) was divided in equal thirds in both the longitudinal and the perpendicular directions to make 9 sections in total. The amount of the adhesive in each section was measured. The weight (average) of the adhesive of each section was divided by the designed area of the section to obtain the basis weight of each section. A percent deviation of the measured basis weight from the designed basis weight was calculated, and the difference between the maximum deviation and the minimum deviation of the 9 sections was taken as the variation width. The uniformity of the amount of applied adhesive per unit area was evaluated based on the variation width and rated as follows.

A: The variation width is within 10%.
B: The variation width is more than 10% and within 15%.
C: The variation width is more than 15% and within 20%.
D: The variation width is more than 20%.

(3) Pattern Clarity

A film having higher release properties than the release paper was stuck to the adhesive applied side of the release paper and rolled together. The pattern of the adhesive adhered to the film was evaluated with the naked eye and rated as follows.

A: No voids are observed in the solid part of the pattern. The outline is evenly clear all over the pattern.
B: No evident voids are observed in the solid part of the pattern. Voids, if any, are not larger than 2 mm.
C: Voids larger than 2 mm and smaller than 5 mm are observed in the solid part of the pattern.
D: Voids of 5 mm or larger are observed in the solid part of the pattern.

The results of evaluation in Examples 1 and 2 and Comparative Example 1 are shown in Table 1. Table 2 shows the results of evaluation in Examples 3 to 5 together with the results of Comparative Example 1.

TABLE 1

|  |  | Example 10 | Example 20 | Comparative Example 1 |
|---|---|---|---|---|
| Dimension (mm) | L1 | 130.7 | 131.9 | 130.0 |
|  | W2 | 43 | 43.8 | 37.5 |
| Dimensional Ratio to | L1 | 100.5 | 101.5 | 100.0 |
| Designed Values (%) | W2 | 102.4 | 104.3 | 101.4 |
| Variation of Amount of Applied Adhesive from Designed Basis Weight (max.-min. in 9 sections) (%) |  | 9.7 | 13.2 | 33.9 |
| Uniformity of Amount of Applied Adhesive |  | A | B | D |
| Pattern Clarity |  | A | B | B |

TABLE 2

|  |  | Example 3 | Example 4 | Example 5 | Comp. Example 1 |
|---|---|---|---|---|---|
| Dimension (mm) | L1 | 130.6 | 130.1 | 132.5 | 130.0 |
|  | W2 | 37.4 | 37 | 38.6 | 37.5 |
| Dimensional Ratio to | L1 | 100.5 | 100.1 | 101.9 | 100.0 |
| Designed Values (%) | W2 | 100.1 | 100.0 | 104.3 | 101.4 |
| Variation of Amount of Applied Adhesive from Designed Basis Weight (max.-min. in 9 sections) (%) |  | 11.6 | 12.5 | 16.6 | 33.9 |
| Uniformity of Amount of Applied Adhesive |  | A | B | C | D |
| Pattern Clarity |  | A | A | B | B |

As shown in Tables 1 and 2, it was confirmed that the adhesive was applied uniformly over the entire area to be coated of the substrate in Examples 1 to 5 as compared with Comparative Example 1.

INDUSTRIAL APPLICABILITY

The liquid applicator according to the first aspect of the present invention enables uniformly applying a liquid such as an adhesive to a substrate in a prescribed pattern over the entire area to be coated of the substrate. It enables applying a liquid in a fine and complicated pattern.

The liquid applicator according to the second aspect of the present invention enables uniformly applying a liquid such as an adhesive.

According to the method of producing an absorbent article according to the invention, an adhesive is uniformly applied to a desired area, allowing for efficiently manufacturing high quality absorbent articles.

The invention claimed is:

1. A method of producing an absorbent article having, on its side to be brought into contact with a garment, a pressure-sensitive adhesive layer formed by applying an adhesive and being adapted to be attached to the garment via the pressure-sensitive adhesive layer,
the method comprising the step of applying an adhesive to a sheet material providing the side to be brought into contact with a garment by using a liquid applicator, wherein
the liquid applicator comprises a discharge roller that discharges a liquid fed from feeding means in a prescribed pattern and being configured to apply the liquid discharged from the discharge roller to a moving substrate,
the discharge roller comprising a surface plate as an outer peripheral portion thereof and a roller main body as a portion radially inward of the surface plate,
the roller main body having in an outer peripheral portion thereof a recess of prescribed shape, in which a liquid introduced therein through inside the roller main body is adapted to spread along a surface of the surface plate,
the surface plate having, in the portion thereof covering the recess, a liquid exit part that permits exit of a liquid in a pattern different from the opening shape of the recess and a liquid, block part that blocks passage of a liquid, and
the liquid exit part being formed of a porous material having a large number of fine pores,
wherein the liquid is an adhesive,
where the fine pores of the porous material are smaller than the liquid exit part,
wherein the surface plate comprises a pattern plate having a hole different in shape from the opening of the recess and a porous plate having a large number fine pores, the porous plate being superposed on the pattern plate to cover the hole,
wherein the porous plate provides the outermost surface of the discharge roller, and
the adhesive is applied to a sheet material thought the hole of the pattern plate and the porous plate so that the adhesive is formed in a shape of the hole of the pattern plate or the sheet material.

2. The method of producing an absorbent article according to claim 1, further comprising the steps of applying an adhesive to a component of the absorbent article by using the liquid applicator and joining the component to other component via the adhesive.

3. The method of producing an absorbent article according to claim 1, wherein the number of the fine pores per liquid exit part is at least 3.

4. The method of producing an absorbent article according to claim 1, wherein an overall thickness of the surface plate is smaller than a depth of the recess of the roller main body.

* * * * *